United States Patent [19]
Wos et al.

[11] Patent Number: 5,977,173
[45] Date of Patent: Nov. 2, 1999

[54] AROMATIC $C_{16}$-$C_{20}$-SUBSTITUTED TETRAHYDRO PROSTAGLANDINS USEFUL AS FP AGONISTS

[76] Inventors: John August Wos; Mitchell Anthony deLong; Jack S. Amburgey, Jr.; Biswanath De, all of The Procter Gamble Company 8700 Mason-Montgomery Rd., Mason, Ohio 45040-9462; Haiyan George Dai, 47-2 Revere Rd., Drexel Hill, Pa. 19026; Yili Wang, 8700 Mason-Montgomery Rd., Mason, Ohio 45040-9462

[21] Appl. No.: 09/148,006

[22] Filed: Sep. 4, 1998

Related U.S. Application Data

[60] Provisional application No. 60/058,217, Sep. 9, 1997.

[51] Int. Cl.⁶ ........................ C07C 405/00; A01K 31/557
[52] U.S. Cl. ........................ 514/530; 514/562; 514/567; 514/570; 549/66; 560/12; 560/16; 560/17; 560/43; 562/429; 562/431; 562/457; 562/64; 564/99
[58] Field of Search ................... 560/121, 12, 16, 560/17, 43; 562/431, 429, 457, 621; 514/530, 562, 567, 570; 549/66; 564/99

[56] References Cited

U.S. PATENT DOCUMENTS

| | | | |
|---|---|---|---|
| 3,776,938 | 12/1973 | Bergstrom et al. | 260/468 |
| 3,966,792 | 6/1976 | Hayashi et al. | 260/468 |
| 4,004,020 | 1/1977 | Skuballa et al. | 424/278 |
| 4,011,262 | 3/1977 | Hess | 560/118 |
| 4,024,179 | 5/1977 | Bindra et al. | 260/473 |
| 4,051,238 | 9/1977 | Sokolowski | 424/181 |
| 4,073,934 | 2/1978 | Skuballa et al. | 424/305 |
| 4,128,720 | 12/1978 | Hayashi et al. | 560/9 |
| 4,154,950 | 5/1979 | Nelson | 560/53 |
| 4,206,151 | 6/1980 | Grudzinskas | 568/367 |
| 4,621,100 | 11/1986 | Lund et al. | 514/573 |
| 5,166,178 | 11/1992 | Ueno et al. | 514/573 |
| 5,212,324 | 5/1993 | Ueno | 554/118 |
| 5,296,504 | 3/1994 | Stjernschantz et al. | 514/573 |
| 5,302,617 | 4/1994 | Ueno | 514/573 |
| 5,321,128 | 6/1994 | Stjernschantz et al. | 514/530 |
| 5,332,730 | 7/1994 | Chan | 511/151 |
| 5,409,911 | 4/1995 | Tyler et al. | 514/91 |
| 5,422,368 | 6/1995 | Stjernschantz | 514/530 |
| 5,422,369 | 6/1995 | Stjernschantz | 514/530 |
| 5,426,115 | 6/1995 | Ueno et al. | 514/438 |
| 5,578,618 | 11/1996 | Stjernschantz | 514/365 |
| 5,587,391 | 12/1996 | Burk | 514/357 |
| 5,627,208 | 5/1997 | Stjernschantz et al. | 514/530 |
| 5,665,773 | 9/1997 | Klimko et al. | 514/530 |
| 5,688,819 | 11/1997 | Woodward et al. | 514/357 |
| 5,703,108 | 12/1997 | Cameron et al. | 514/382 |
| 5,834,498 | 11/1998 | Burk | 514/445 |

FOREIGN PATENT DOCUMENTS

| | | |
|---|---|---|
| 0 857 718 A1 | 6/1997 | European Pat. Off. . |
| 002 460 990 | 7/1976 | Germany . |
| WO 92/02495 | 2/1992 | Germany . |
| WO 98/12175 | 3/1998 | Japan . |
| 1 456 838 | 11/1972 | United Kingdom . |
| 1 542 569 | 8/1976 | United Kingdom . |
| WO 95/18102 | 7/1995 | WIPO . |
| WO 97/23225 | 7/1997 | WIPO . |
| WO 97/31895 | 9/1997 | WIPO . |
| WO 98/20880 | 5/1998 | WIPO . |
| WO 98/20881 | 5/1998 | WIPO . |
| WO 98/21180 | 5/1998 | WIPO . |
| WO 98/50024 | 11/1998 | WIPO . |

OTHER PUBLICATIONS

Liljebris, C., Selen, G., Resul, B., Stjernschantz, J., and Hacksell, U., "Dervatives of 17–Phenyl–18, 19, 20–trinor-prostaglandin $F_{2\alpha}$ Isoppropyl Ester: Potential Antiglaucoma Agents", *Journal of Medicinal Chemistry*, vol. 38, No.2, (1995).

Bundy, G. L., and Lincoln, F. H., "Synthesis of 17–Phenyl–18, 19, 20–Trinoprostaglandins I. The $PG_1$ Series", *Prostaglandins*, vol. 9, No. 1, (Jan. 1975).

*Primary Examiner*—Robert Gerstl
*Attorney, Agent, or Firm*—James C. Kellerman; Carl J. roof; Mary Pat McMahon

[57] ABSTRACT

The invention provides novel PGF analogs. In particular, the present invention relates to compounds having a structure according to the following formula:

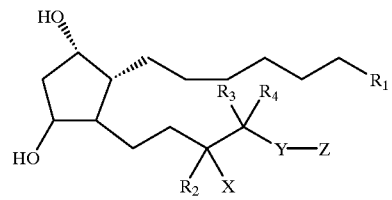

wherein $R_1$, $R_2$, $R_3$, $R_4$, X, Y, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

28 Claims, No Drawings

AROMATIC $C_{16}$-$C_{20}$-SUBSTITUTED TETRAHYDRO PROSTAGLANDINS USEFUL AS FP AGONISTS

CROSS REFERENCE

This application claims priority under Title 35, United States Code 119(e) from Provisional Application Ser. No. 60/058,217, filed Sep. 9, 1997.

TECHNICAL FIELD

The subject invention relates to certain novel analogs of the naturally occurring prostaglandin. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandin (PGA, PGB, PGE, PGF, and PGI) are C-20 unsaturated fatty acids. $PGF_{2\alpha}$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_{2\alpha}$ has the following formula:

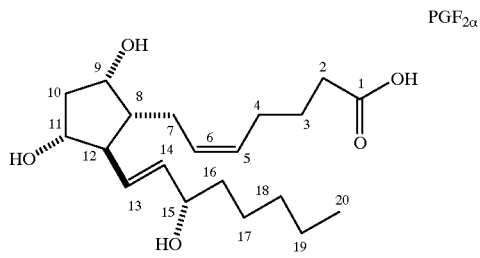

$PGF_{2\alpha}$

Analogs of naturally occurring Prostaglandin F have been disclosed in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.* Vol. 93 (1993), pp. 1533–1564; G. L. Bundy and F. H. Lincoln, "Synthesis of 17-Phenyl-18,19,20-Trinorprostaglandins: I. The $PG_1$ Series", *Prostaglandin*, Vol. 9 No. 1 (1975), pp. 1–4; W. Bartman, G. Beck, U. Lerch, H. Teufel, and B. Scholkens, "Luteolytic Prostaglandin: Synthesis and Biological Activity", *Prostaglandin*, Vol. 17 No. 2 (1979), pp. 301–311; C. Iiljebris, G. Selen, B. Resul, J. Sternschantz, and U. Hacksell, "Derivatives of 17-Phenyl-18, 19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Naturally occurring prostaglandin are known to possess a wide range of pharmacological properties. For example, prostaglandin have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandin are characterized by their activity against a particular prostaglandin receptor, they generally are not specific for any one prostaglandin receptor. Therefore, naturally-occurring prostaglandin are known to cause side effects such as inflammation, as well as surface irritation when administered systemically. It is generally believed that the rapid metabolism of the naturally occurring prostaglandin following their release in the body limits some of the effects of the prostaglandin to a local area. This effectively prevents the prostaglandin from stimulating prostaglandin receptors throughout the body and causing the effects seen with the systemic administration of naturally occurring prostaglandin.

Prostaglandin, especially prostaglandin of the E series (PGE), are known to be potent stimulators of bone resorption. $PGF_{2\alpha}$ has also been shown to be a stimulator of bone resorption but not as potent as $PGE_2$. Also, it has been demonstrated the $PGF_{2\alpha}$ has little effect on bone formation. It has been suggested that some of the effects of $PGF_{2\alpha}$ on bone resorption, formation and cell replication may be mediated by an increase in endogenous $PGE_2$ production.

In view of both the wide range of pharmacological properties of naturally occurring prostaglandin and of the side effects seen with the systemic administration of these naturally occurring prostaglandin, attempts have been made to prepare analogs to the naturally occurring prostaglandin that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

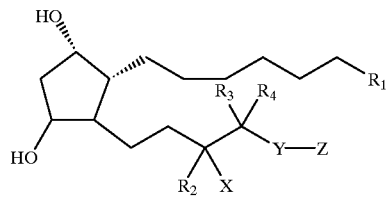

wherein $R_1$, $R_2$, $R_3$, $R_4$, X, Y, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

DETAILED DESCRIPTION OF THE INVENTION

Terms and Definitions

"Acyl" is a group suitable for acylating a nitrogen atom to form an amide or carbamate or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to about 4 substituents. Preferred alkyl are unsubstituted. Preferred substituted alkyl are mono-, di-, or trisubstituted. Preferred alkyl substituents include halo, hydroxy, aryl (e.g., phenyl, tolyl, alkyloxphenyl, alkyloxycarbonylphenyl, halophenyl), heterocyclyl, and heteroaryl.

"Aromatic ring" is an aromatic hydrocarbon ring system. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to about 4 substituents on the ring. Preferred aromatic ring substituents include: halo, cyano, alkyl, heteroalkyl, haloalkyl, phenyl, phenoxy or any combination thereof. More preferred substituents include halo and haloalkyl. Preferred aromatic rings include naphthyl and phenyl. The most preferred aromatic ring is phenyl.

"Bone disorder" means the need for bone repair or replacement. Conditions in which the need for bone repair or replacement may arise include: osteoporosis (including post menopausal osteoporosis, male and female senile osteoporosis and corticosteroid induced osteoporosis), osteoarthritis, Paget's disease, osteomalacia, multiple myeloma and other forms of cancer, prolonged bed rest, chronic disuse of a limb, anorexia, microgravity, exogenous and endogenous gonadal insufficiency, bone fracture, non-union, defect, prosthesis implantation and the like.

"Carbocyclic aliphatic ring" is a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to about 4 substituents on the ring. Preferred carbocyclic aliphatic ring substituents include: halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl. The most preferred carbocyclic aliphatic ring is cycloheptyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1$–$C_{12}$; more preferred are $C_1$–$C_6$; more preferred still are $C_1$–$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents. Preferred heteroalkyl are unsubstituted. Preferred heteroalkyl substituents include halo, hydroxy, aryl (e.g., phenyl, tolyl, alkyloxphenyl, alkyloxycarbonylphenyl, halophenyl), heterocyclyl, heteroaryl. For example, alkyl substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di- $C_1$–$C_3$ alkanylamino, methylphenylamino, methylbenzylamino, $C_1$–$C_3$ alkanylamido, carbamamido, ureido, guanidino).

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include: halo, cyano, alkyl, heteroalkyl, haloalkyl, phenyl, phenoxy or any combination thereof. More preferred substituents include halo and haloalkyl. Preferred heterocyclic aliphatic rings include piperzyl, morpholinyl, tetrahydrofuranyl, tetrahydropyranyl and piperdyl.

"Heteroaromatic ring" is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 member atoms in the ring. Bicyclic heteroaromatic rings contain from 8 to 12 member atoms, preferably 9 or 10 member atoms in the ring. Heteroaromatic rings may be unsubstituted or substituted with from 1 to about 4 substituents on the ring. Preferred heteroaromatic ring substituents include: halo, cyano, alkyl, heteroalkyl, haloalkyl, phenyl, phenoxy or any combination thereof. More preferred substituents include halo, haloalkyl, and phenyl. Preferred heteroaromatic rings include thienyl, thiazolo, purinyl, pyrimidyl, pyridyl, and furanyl. More preferred heteroaromatic rings include thienyl, furanyl, and pyridyl. The most preferred heteroaromatic ring is thienyl.

"Lower alkyl" is an alkyl chain radical comprised of 1 to 6, preferably 1 to 4 carbon atoms.

"Phenyl" is a six-membered monocyclic aromatic ring which may or may not be substituted with from about 1 to about 4 substituents. The substituents may be substituted at the ortho, meta or para position on the phenyl ring, or any combination thereof. Preferred phenyl substituents include: halo, cyano, alkyl, heteroalkyl, haloalkyl, phenyl, phenoxy or any combination thereof. More preferred substituents on the phenyl ring include halo and haloalkyl. The most preferred substituent is halo. The preferred substitution pattern on the phenyl ring is ortho or meta. The most preferred substitution pattern on the phenyl ring is ortho.

Compounds

The subject invention involves compounds having the following structure:

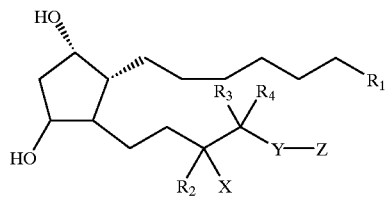

In the above structure, $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring. Preferred $R_5$ is $CH_3$, $C_2H_5$, $C_3H_7$. Preferred $R_1$ is $CO_2H$, $C(O)NHOH$, $CO_2CH_3$, $CO_2C_2H_5$, $CO_2C_3H_7$, $CO_2C_4H_9$, $CO_2C_3H_7O_2$, and $C(O)NHS(O)_2R_5$. More preferred $R_1$ is $CO_2H$, $C(O)NHOH$, $CO_2CH_3$, and $CO_2C_3H_5$. Most preferred $R_1$ is $CO_2H$ and $CO_2CH_3$.

In the above structure, $R_2$ is H or lower alkyl. Preferred $R_2$ is H and $CH_3$. Most preferred $R_2$ is H.

In the above structure, X is $NR_6R_7$, $OR_8$, $SR_9$, $S(O)R_9$, or $S(O)_2R_9$; wherein $R_6,R_7$, and $R_8$ are independently selected from the group consisting of H, acyl, alkyl, heteroalkyl, carbocyclic aliphatic ring, heterocyclic aliphatic ring, aromatic ring, and heteroaromatic ring; and wherein $R_9$ is alkyl, heteroalkyl, carbocyclic aliphatic ring, heterocyclic aliphatic ring, aromatic ring, or heteroaromatic ring. Preferred $R_6$ and $R_7$ are H, $CH_3$ and $C_2H_5$. Preferred $R_8$ is H, $CH_3$, $C_2H_5$ and $C_3H_7$. Preferred $R_9$ is $CH_3$ and $C_2H_5$. Preferred X is $NR_6R_7$ and $OR_8$. Most preferred X is OH.

In the above structure, $R_3$ and $R_4$ are independently selected from the group consisting of H, $CH_3$, and $C_2H_5$. Preferred $R_3$ and $R_4$ are H.

In the above structure, Y is $NR_{10}$, S, S(O), or $S(O)_2$; wherein $R_{10}$ is H, acyl, alkyl, heteroalkyl, carbocyclic aliphatic ring, heterocyclic aliphatic ring, aromatic ring, or heteroaromatic ring. Preferred $R_{10}$ is H and $CH_3$. Preferred Y is NH and S.

In the above structure, Z is carbocyclic aliphatic ring, heterocyclic aliphatic ring, aromatic ring, or heteroaromatic ring. Preferred Z is monocyclic carbocyclic aliphatic ring, monocyclic heterocyclic aliphatic ring, monocyclic aromatic ring, and monocyclic heteroaromatic ring. More preferred Z is monocyclic aromatic ring or monocyclic heteroaromatic ring. The most preferred Z is thienyl or phenyl.

The invention also includes optical isomers, diastereomers and enantiomers of the above structure. Thus, at all stereocenters where stereochemistry is not defined ($C_{11}$, $C_{12}$, $C_{15}$, and $C_{16}$), both epimers are envisioned. Preferred stereochemistry at all such stereocenters of the compounds of the invention mimic that of naturally occurring $PGF_{2\alpha}$.

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turnover rate; and (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. Iiijebris, G. Selen, B. Resul, J. Sternschantz, and U. Hacksell, "Derivatives of 17-Phenyl-18,19,20-trinorprostaglandin $F_2\alpha$ Isopropyl Ester: Potential Antiglaucoma Agents", *Journal of Medicinal ChemistrY*, Vol. 38 No. 2 (1995), pp. 289–304.

Compounds useful in the subject invention can be made using conventional organic syntheses. A particularly preferred synthesis is the following general reaction scheme:

Scheme 1

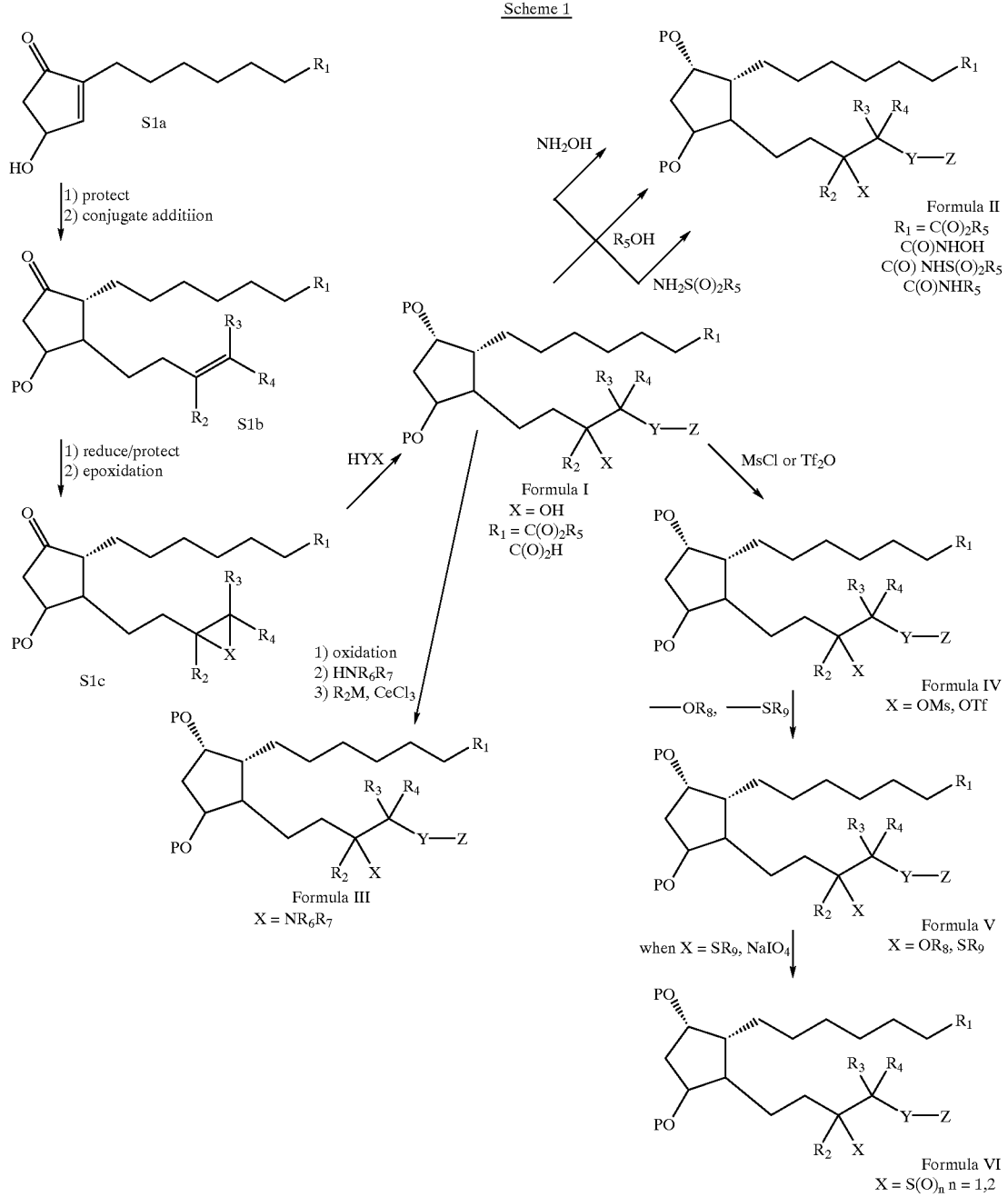

In Scheme 1, $R_1$, $R_2$, $R_3$, $R_4$, X, Y, and Z are as defined above. The Methyl 7-[3-(R)-hydroxy-5-oxo-1-cyclopent-1-yl] heptanoate (S1a) depicted as starting material for Scheme 1 is commercially available (such as from Sumitomo Chemical or Cayman Chemical).

In the above Scheme 1, Methyl 7-[3-(R)-hydroxy-5-oxo-1-cyclopent-1-yl] heptanoate (S1a) is reacted with a silylating agent and base in a solvent that will allow the silylation to proceed. Preferred silylating agents include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichloromethane being the most preferred solvent. The reaction is allowed to proceed at a temperature preferably between -100° C. and 100° C., more preferably between -80° C. and 80° C., and most preferably between -70° C. and 23° C.

The resulting silylated compound is isolated by methods known to those of ordinary skill in the art. Such methods include, but are not limited to, extraction, solvent evaporation, distillation, and crystallization. Preferably, the silyl ether is purified after isolation by distillation under vacuum.

The silylated compound is then reacted with the cuprate generated via Grignard formation of the appropriate alkenyl bromide as disclosed, for example, in the following references: H. O. House et. al., "The Chemistry of Carbanions: A Convenient Precursor for the Generation of Lithium Organocuprates", *J. Org. Chem.* Vol. 40 (1975) pp. 1460–69 and P. Knochel et. al., "Zinc and Copper Carbenoids as Efficient and Selective a'/d' Multicoupling Reagents", *J. Amer.Chem. Soc.* Vol. 111 (1989) p. 6474–76. Preferred alkenyl bromides include 4-bromo-1-butene, 4-bromo-1-butyne, 4-bromo-2-methyl-1-butene, and 4-bromo-2-ethyl-1-butene. The most preferred alkenyl bromide is 4-bromo-1-butene. Preferred solvents include ethereal solvents, of which diethyl ether and tetrahydrofuran are preferred. The most preferred solvent is tetrahydrofuran. The Grignard reagent is allowed to form at a temperature between 100° C. and 23° C., more preferably between 85° C. and 30° C., and most preferably between 75° C. and 65° C. The reaction time is preferably between 1 hour and 6 hours, with a more preferred reaction time being between 2 hours and 5 hours, and the most preferred reaction time being between 3 hours and 4 hours.

Once the Grignard reagent is formed, the cuprate is generated from the alkenyl magnesium species. The temperature range for cuprate formation is between −100° C. and 0° C. The preferred temperature range is between −80° C. and −20° C. The more preferred temperature range is between −75° C. and −50° C. The preferred reaction time is between 30 minutes and 6 hours. The more preferred reaction time is between 45 minutes and 3 hours. The most preferred reaction time is between 1 hours and 1.5 hours.

The compound depicted as S1b is isolated by methods known to one of ordinary skill in the art. Such methods include, but are not limited to, extraction, solvent evaporation, distillation, and crystallization. Preferably, S1b is purified by flash chromatography on silica gel (Merck, 230–400 mesh) using 10% EtOAc/hexanes as the eluent.

S1b is then reacted with a hydride reducing agent and a polar, protic solvent to give the Cg alcohol. Preferred reducing agents include lithium aluminum hydride, sodium borohydride, and L-selectride. More preferred reducing agents include sodium borohydride, and L-selectride. The most preferred reducing agent is sodium borohydride. Preferred solvents include methanol, ethanol, and butanol. The most preferred solvent is methanol. The reduction is carried out at a temperature between −100° C. and 23° C. The preferred temperature range is between −60° C. and 0° C. The most preferred temperature range is between −45° C. and −20° C.

The resulting alcohol of S1b is isolated by methods known to one of ordinary skill in the art. Such methods include, but are not limited to, extraction, solvent evaporation, distillation, and crystallization. Preferably, the alcohol is purified by flash chromatography on silica gel (Merck, 230–400 mesh) using 20% EtOAc/hexanes as the eluent.

The alcohol can be protected as described previously herein. The protected or unprotected alcohol is then treated with meta-chloroperbenzoic acid in a halocarbon solvent to provide the novel epoxide intermediate depicted as S1c. Preferred halocarbon solvents include dichloromethane, dichloroethane, and chloroform. More preferred halocarbon solvents are dichloromethane and dichloroethane. The most preferred halocarbon solvent is dichloromethane.

The compound depicted as S1c is isolated by methods known to one of ordinary skill in the art. Such methods include, but are not limited to, extraction, solvent evaporation, distillation, and crystallization. Preferably, S1b is purified by flash chromatography on silica gel (Merck, 230–400 mesh) using 20% EtOAc/hexanes as the eluent.

The intermediate epoxide depicted as S1c can be reacted with a variety of oxygen, sulfur and nitrogen containing nucleophiles as disclosed, for example, in J. G. Smith, "Synthetically Useful Reactants of Epoxides", *Synthesis* (1984) p. 629–656, to provide the $C_{11}$-protected 13,14-dihydro-15-substituted-16-tetranor Prostaglandin $F_1$ α derivatives of Formula I.

With sulfur nucleophiles, the reaction is carried out preferably at between 150° C. and 0° C., more preferably between 120° C. and 20° C., and most preferably between 80° C. and 50° C. Preferred bases for the reaction include triethylamine, N,N diisopropylethylamine, and trimethylamine. The most preferred base is triethylamine. Preferred solvents for the reaction are aromatic hydrocarbon solvents. Preferred solvents include xylenes, toluene, and benzene. The most preferred solvent is benzene. With nitrogen and oxygen nucleophiles, preferred solvents include ethereal solvents and polar, protic solvents. More preferred ethereal solvents include diethyl ether, dibutyl ether and tetrahydrofuran. The most preferred ethereal solvent is tetrahydrofuran. More preferred polar, protic solvents include ethyl alcohol, methyl alcohol, and tert-butyl alcohol. The most preferred polar, protic solvent is ethyl alcohol.

The ring-opening process with nitrogen and oxygen nucleophiles can be catalyzed with Lewis acids. Preferred Lewis acids include magnesium perchlorate, trimethylsilyl trifluoromethanesulphonate, and trimethylaluminum. The most preferred Lewis acid is magnesium perchlorate. The reaction is carried out at a temperature between 150° C. and 23° C., preferably between 125° C. and 40° C., and more preferably between 100° C. and 75° C.

The resulting compounds can be isolated, but are generally deprotected using techniques known to one of ordinary skill in the art, and isolated as the final 13,14-dihydro-15-substituted-16-tetranor prostaglandin $F_{1\alpha}$ derivative. Compounds depicted by Formula I are exemplified in Examples 2–28.

Compounds depicted by Formula II can be made directly from those described in Formula I by methods known to one of ordinary skill in the art. For example, the condensation of methyl esters of Formula I with amines or hydroxylamine provides compounds depicted by Formula II. Compounds depicted by Formula II are exemplified in Examples 29–32.

Compounds depicted by Formula IIII can be made directly from those described in Formula I by methods known to one of ordinary skill in the art. The appropriately protected derivative from Formula I is oxidized to the ketone following the process described in the following references: A. McKillop and D. W. Young, "Organic Synthesis Using Supported Reagents—Part 1", *Synthesis* (1979) p. 401–22; G. Piancatelli et al., "Pyridium Chlorochromate: A Versatile Oxidation Organic Synthesis", *Synthesis* (1982) p. 245–58; E. J. Corey and J. W. Suggs, "Pyridinium Chlorochromate: An Efficient Reagent for Oxidation of Primary and Secondary Alcohols to Carbonyl Compounds", *Tetrahedron Lett.* Vol. 31 (1975) p. 2647–50; and references cited therein. The ketone is then condensed with N-methylamine to give the imine. Addition of the methylcerium nucleophile (~1.5 equiv.), as described for example in T. Imamoto, et al., "Carbon-Carbon Bond Forming Reactions Using Cerium Metal or Organcerium (Ill) Reagents", *J. Org. Chem.* Vol. 49 (1984) p. 3904–12; T. Imamoto, et al., "Reactions of Carbonyl Compounds with Grignard Reagents in the Presence of Cerium Chloride", *J. Am. Chem. Soc.* Vol. 111 (1989) p. 4392–98; and references cited therein, gives the aminomethyl derivative of Formula III. Compounds depicted by Formula III are exemplified in Examples 39–42.

Compounds depicted by Formula IV and Formula V can be made from compounds described in Formula I by activation and subsequent nucleophilic displacement of the appropriately functionalized hydroxyl group. Transformations of this type are described in the following references: E. J. Corey et al., "Simple Stereospecific Routes to 9-epi-Prostaglandin $F_2\alpha$", *J.C.S. Chem. Comm.* (1975) p. 658–9; E. J. Corey et al., "Superoxide ion as a Synthetically Useful Oxygen Nucleophile", *Tetrahedron Lett.* (1975) p. 3183–6; E. J. Corey et al., "Total Synthesis of 5-desoxy Leukotriene D. A New and Useful Equivalent of the 4-Formyl-Trans, Trans-1,3-Butadienyl Anion", *Tetrahedron Lett.* Vol. 23 (1982) p. 3463–66; and references cited therein. Compounds depicted by Formula V are exemplified in Examples 33–36.

Compounds depicted by Formula VI can be made from those described in Formula V (where X is $SR_9$) by selective oxidation procedures as described, for example, in the following references: E. J. Corey et al., "Pathways for Migration and Cleavage of the S-Peptide Unit of the Leukotrienes", *Tetrahedron Lett.* Vol. 23 (1982) p. 3467–70; *Prostaglandin* Vol. 24 (1982) p. 801; Y. Girard et al., "Synthesis of the Sulfones of Leukotrienes $C_4$, $D_4$, and $E_4$", *Tetrahedron Lett.* Vol. 23 (1982) p. 1023–26; and references cited therein. Compounds depicted by Formula VI are exemplified in Examples 37–38.

The following non-limiting examples illustrate the compounds, compositions, and uses of the present invention.

Examples Compounds are analyzed using $^1H$ and $^{13}C$ NMR, Elemental analysis, mass spectra, high resolution mass spectra and/or IR spectra as appropriate.

Typically, inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis is performed on glass mounted silica gel plates (200–300 mesh; Baker) and visualized using UV, 5% phosphomolybdic acid in EtOH, or ammonium molybdate/cerric sulfate in 10% aqueous $H_2SO_4$.

Example 1

Preparation of 13,14-dihydro-16-(3-fluorophenylthio) tetranor prostaglandin $F_1\alpha$ (1i), and 13,14-dihydro-15-methyl-16-(3-fluorophenylthio) tetranor prostaglandin $F_1\alpha$ (1j):

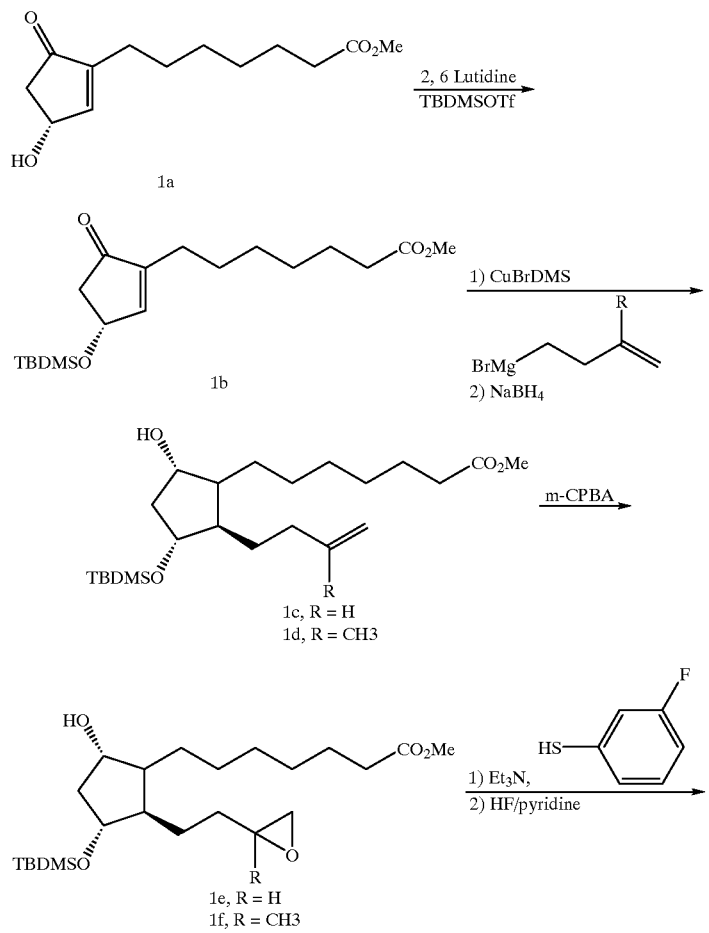

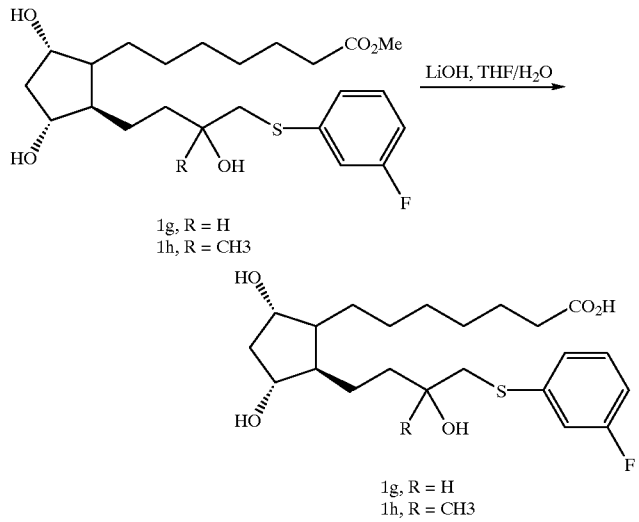

1g, R = H
1h, R = CH3

1g, R = H
1h, R = CH3 a. Methyl 7-(2-oxo-4-(1,1,2,2-tetramethyl-1-silapropoxy) cyclopent-1-enyl) heptanoate 1b: To a solution of Methyl-7-[3-(R)-hydroxy-5-oxo-1-cyclopenten-1-yl] heptanoate 1a (1 equiv.) in $CH_2Cl_2$ at −78° C. is added 2,6 Lutidine (1.3 equiv.) dropwise over 15 minutes. The solution is kept at −78° C., and TBDMS Triflate (1.2 equiv.) in $CH_2Cl_2$ is added dropwise over 15 minutes. The reaction is warmed gradually to room temperature and stirred at room temperature for 15 hours. Aqueous 10% HCl is added and the layers are separated. The water layer is extracted with $CH_2Cl_2$ and the organic layers are combined. The organic layer is washed with brine, dried ($Na_2SO_4$) and concentrated. The residue is distilled under vacuum (10 mm Hg) to provide the silyl ether 1b as a yellow liquid.

b. Methyl 7-(5-but-3-enyl-2-hydroxy-4-(1,1,2,2-tetramethyl-1-silapropoxy)cyclopentyl) heptanoate 1c, 1d: To a slurry of $Mg^0$ powder (2 equiv.) in THF at room temperature is added one crystal of $I_2$ and 1-bromobutene (2 equiv.) dropwise over 10 minutes. The reaction proceeds to exotherm as the addition continues. After the addition is complete, the reaction is refluxed for 3 hours and cooled to room temperature. The Grignard is diluted with THF and added via cannula to a 3-necked flask equipped with mechanical stirring and charged with CuBr.DMS (2 equiv.) in a 1:1 solution of THF/DMS at −78° C. After the addition of the Grignard (~20 min), the reaction is stirred for 1 hour at −78° C. The color of the reaction is dark red at this point. A solution of the ketone 1b (1 equiv.) in THF is then added dropwise over 25 minutes. The reaction is stirred at −78° C. for 15 minutes, then allowed to warm slowly to room temperature over 2 hours. The reaction is quenched with aqueous $NH_4Cl$ and the excess DMS is allowed to evaporate overnight. The reaction is partitioned between brine/$CH_2Cl_2$ and the layers are separated. The aqueous layer is back-extracted with $CH_2Cl_2$ and the organic layers are combined and dried ($Na_2SO_4$). The solvent is removed in vacuo and the residue is chromatographed on $SiO_2$ (10% hexane/EtOAc) to give the ketone precursor to 1c as a clear oil. The ketone precursor to 1d is prepared in substantially the same manner.

The ketone precursor to 1c (1 equiv.) is dissolved in MeOH and cooled to −40° C. Sodium borohydride (0.9 equiv.) is added portionwise over 10 minutes. After the addition is complete, the reaction is stirred for 13 hours at −40° C. and then for 12 hours at −78° C. The reaction is quenched with water, partitioned between brine and $CH_2Cl_2$, and the layers separated. The aqueous layer is back-extracted with $CH_2Cl_2$ and the organic layers are combined and dried ($Na_2SO_4$). The solvent is removed in vacuo and the residue chromatographed on $SiO_2$ (30% EtOAc/hexanes) to give the alcohol 1c as a colorless oil. Alcohol 1d is prepared in substantially the same manner.

C. Methyl 7-(2-hydroxy-5-(2-(2-oxiranyl)ethyl-4-(1,1,2,2-tetramethyl-1-silapropoxy)cyclopentyl) heptanoate 1e, 1f: The alcohol 1c (1 equiv.) is dissolved in $CH_2Cl_2$ and cooled to 0° C. Sodium bicarbonate is added, followed by m-CPBA (57%–85% purity) (3 equiv.) portionwise over 15 minutes. After the addition is complete, the reaction is stirred for 20 hours at room temperature. The reaction is poured into water, partitioned between brine and $CH_2Cl_2$, and the layers are separated. The aqueous layer is back-extracted with $CH_2Cl_2$ and the organic layers are combined and dried ($Na_2SO_4$). The solvent is removed in vacuo and the residue is chromatographed on $SiO_2$ (20% EtOAc/hexanes) to give the epoxide diasteriomers 1e as a colorless oil. Compound 1f is synthesized in substantially the same manner.

d. 13,14-dihydro-16-(3-fluorophenylthio) tetranor prostaglandin $F_1\alpha$ (1g), and 13,14-dihydro-15-methyl-16-(3-fluorophenylthio) tetranor prostaglandin $F_1\alpha$ (1h) methyl esters: In a 5 mL round-bottomed flask, epoxide 1e (1 equiv.) and 100 uL of dry benzene are added. The flask is cooled to 0° C., then is treated with 60 uL of 3-fluoro thiophenol (1.2 eq) and 78 uL of triethyl amine (1.2 eq) as disclosed in J. G. Smith, "Synthetically Useful Reactants of Epoxides", *Synthesis* (1984) p. 629–656, and references cited therein. The ice bath is removed and the reaction is stirred at room temperature under nitrogen overnight. TLC is used to monitor the reaction. Excess thiophenol is added if necessary. The reaction is quenched with brine and is extracted with methylene chloride. The organic layer is washed three times with 1N HCl, brine, dried over sodium sulfate, and concentrated. Without further purification to this crude reaction mixture, 3 mL of $CH_3CN$ and 0.1 mL of HF/Pyridine (0.1 mmol) are added while the flask is kept at 0° C. After 3 hours at 0° C., the reaction is quenched with saturated NaCl. The aqueous layer is extracted three times with $CH_2Cl_2$. The organic layers are combined and washed three time with 1N HCl, brine, and dried ($Na_2SO_4$). After column chromatography, (7:3, Hexane: Ethyl Acetate) the clear oil 1g is obtained. The ester 1h is prepared in substantially the same manner.

e. 13,14-dihydro-16-(3-fluorophenylthio) tetranor prostaglandin $F_1\alpha$ (1i), and 13,14-dihydro-15-methyl-16-(3-fluorophenylthio) tetranor prostaglandin $F_1\alpha$ (1j): To a 5 ml round-bottomed flask, 50 mg (0.12 mmol) of 13,14-dihydro-16-(3-fluorophenylthio) tetranor Prostaglandin $F_1\alpha$ methyl ester 1 g and 4 mL of THF water solution (3:1, THF:$H_2O$) are added, and the flask is cooled at 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic layers are combined and washed with brine, dried ($Na_2SO_4$), concentrated in vacuo, and the residue is chromatographed (methylene chloride, methanol, acetic acid, 9.6, 0.4, 0.015), to provide 30 mg of the clear oil 1i. The acid 1j is prepared in substantially the same manner.

Utilizing substantially the method of Example 1 (and using the appropriate thiophenol), the following subject compounds of Examples 2–23 are obtained.

Example 2
13,14-dihydro-16-(phenylthio) tetranor Prostaglandin $F_1\alpha$ methyl ester

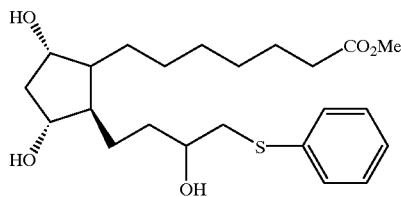

Example 3
13,14-dihydro-16-(3-methylphenylthio) tetranor Prostaglandin $F_1\alpha$ methyl ester

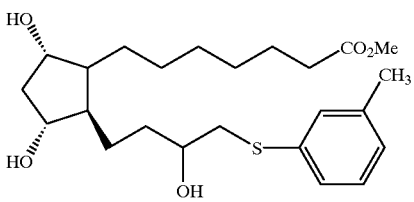

Example 4
13,14-dihydro-16-(3-trifluoromethylphenylthio) tetranor Prostaglandin $F_1\alpha$ methyl ester

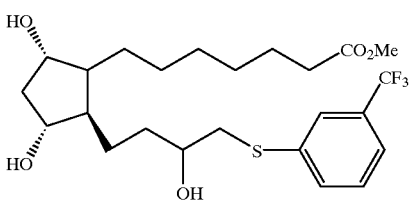

Example 5
13,14-dihydro-16-(2,3,5,6-tetrafluorophenylthio) tetranor Prostaglandin $F_1\alpha$ methyl ester

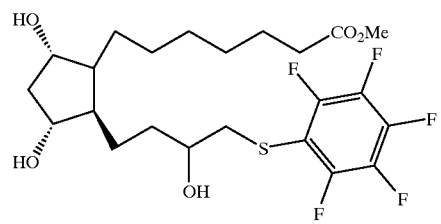

Example 6
13,14-dihydro-16-(2-methylphenylthio) tetranor Prostaglandin $F_1\alpha$ methyl ester

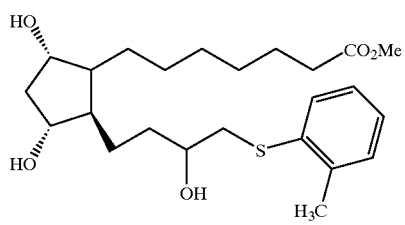

Example 7
13,14-dihydro-16-(4-methylphenylthio) tetranor Prostaglandin $F_1\alpha$ methyl ester

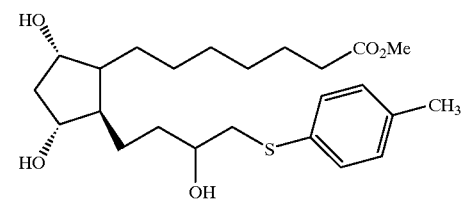

Example 8
13,14-dihydro-16-(2-fluorophenylthio) tetranor Prostaglandin $F_1\alpha$ methyl ester

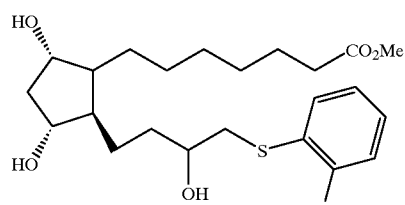

Example 9
13,14-dihydro-15-methyl-16-(phenylthio) tetranor Prostaglandin $F_1\alpha$ methyl ester

Example 10
13,14-dihydro-15-methyl-16-(2-methylphenylthio) tetranor Prostaglandin $F_1\alpha$ methyl ester

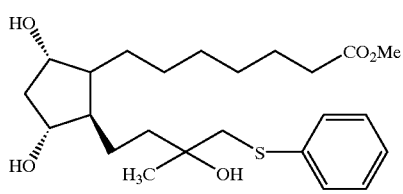

Example 11
13,14-dihydro-16-(2-thienylthio) tetranor prostaglandin $F_1\alpha$ methyl ester

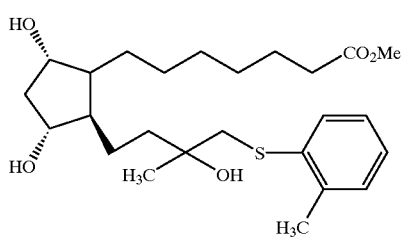

Example 12
13,14-dihydro-16-(phenylthio) tetranor Prostaglandin $F_1\alpha$

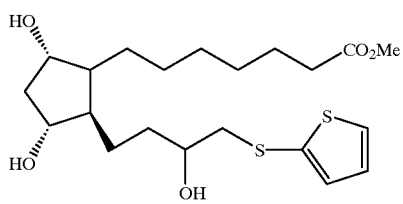

Example 13
13,14-dihydro-16-(3-methylphenylthio) tetranor Prostaglandin $F_1\alpha$

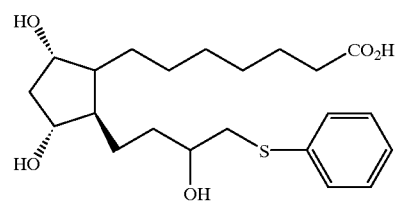

Example 14
13,14-dihydro-16-(3-trifluoromethylphenylthio) tetranor Prostaglandin $F_1\alpha$

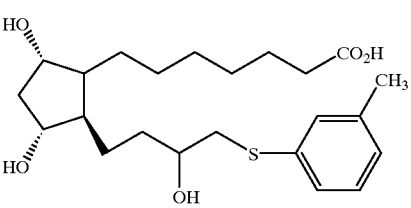

Example 15
13,14-dihydro-16-(2,3,5,6-tetrafluorophenylthio) tetranor Prostaglandin $F_1\alpha$

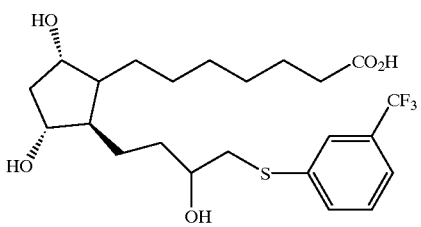

Example 16
13,14-dihydro-15-methyl-16-(2-methylphenylthio) tetranor Prostaglandin $F_1\alpha$

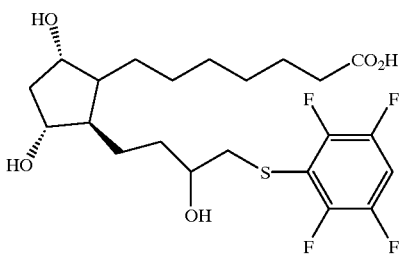

Example 17
13,14-dihydro-16-(4-methylphenylthio) tetranor Prostaglandin $F_1\alpha$

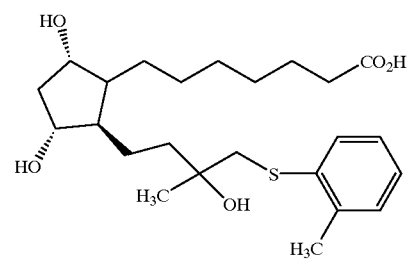

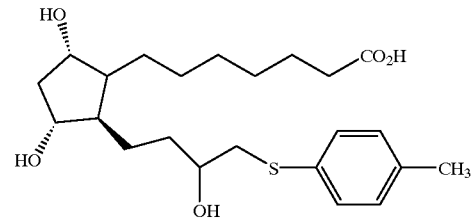

Example 18

13,14-dihydro-16-(1-napthylthio) tetranor Prostaglandin $F_1\alpha$

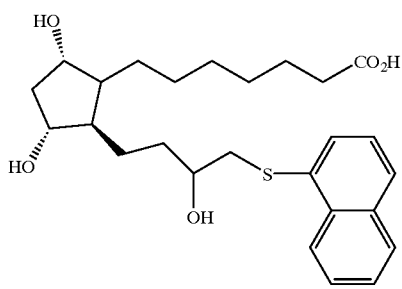

Example 19

13,14-dihydro-16-(cyclohexylthio) tetranor Prostaglandin $F_1\alpha$

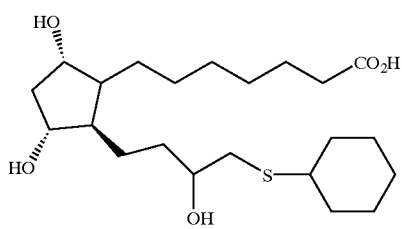

Example 20

13,14-dihydro-16-(2-fluorophenylthio) tetranor Prostaglandin $F_1\alpha$

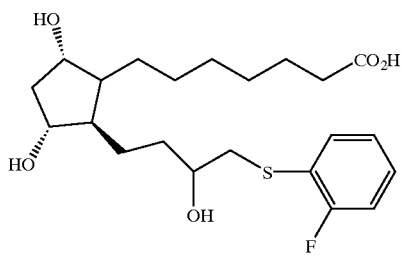

Example 21

13,14-dihydro-15-methyl-16-(phenylthio) tetranor Prostaglandin $F_1\alpha$

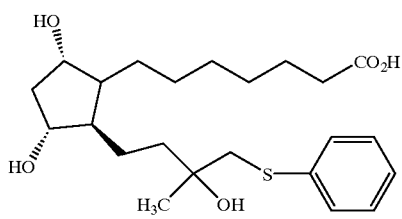

Example 22

13,14-dihydro-15-methyl-16-(3-methylphenylthio) tetranor Prostaglandin $F_1\alpha$

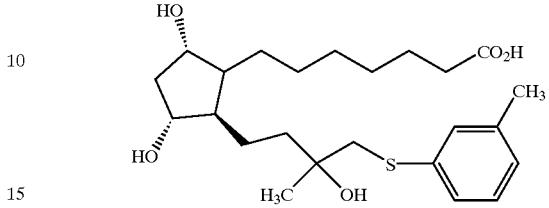

Example 23

13,14-dihydro-16-(3-fluorophenylsulfonyl) tetranor Prostaglandin $F_1\alpha$:

To a solution of 13,14-dihydro-16-(3-fluorophenylthio) tetranor Prostaglandin $F_1\alpha$ (1 equiv.) in $CHCl_3$ at $-78°$ C. is added peracetic acid (2 equiv.) dropwise. The solution is kept at $-78°$ C. for 1 hour, then it is allowed to warm to $0°$ C. and is kept at $0°$ C. for 1 hour. Saturated NaCl is added and the layers are separated. The water layer is extracted with $CH_2Cl_2$ and the organic layers are combined. The organic layer is washed with brine, dried ($Na_2SO_4$) and concentrated. The residue is chromatographed on $SiO_2$ (96 $CH_2Cl_2$, 4 MeOH, 0.1 Acetic acid) to give 13,14-dihydro-16-(3-fluorophenylsulfonyl) tetranor Prostaglandin $F_1\alpha$ as a clear oil.

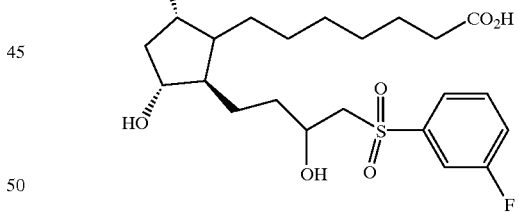

Example 24

Preparation of 13,14-dihydro-16-(3-methylphenylamino) tetranor prostaglandin $F_1\alpha$ methyl ester:

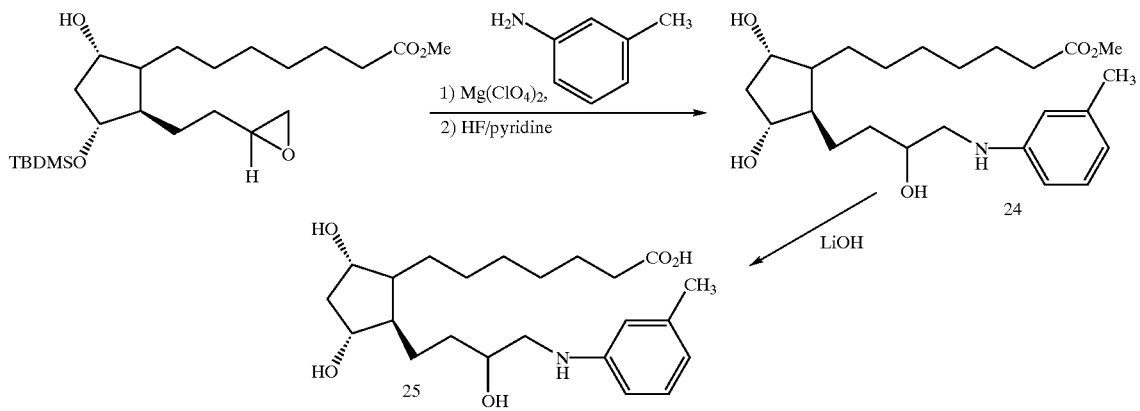

To a 10 mL round-bottomed flask, epoxide 1e (1.26 mmol), m-Toludine (1.5 equiv.), 10 mg of magnesium perchlorate and 2 mL THF are added, after which the reaction is refluxed under nitrogen overnight. The flask is cooled to room temperature and the solvent removed in vacuo. Without further purification of this crude reaction mixture, 3 mL of $CH_3CN$ and 0.5 mL of HFlPyridine (0.5mmol, 0.6 equiv.) are added while the flask is kept at 0° C. After 5 hours at 0° C., the reaction is quenched with saturated NaCl. The aqueous layer is extracted three times with $CH_2Cl_2$. The organic layers are combined and washed three time with saturated $NaHCO_3$, brine, and dried ($Na_2SO_4$). After column chromatography (95% $CH_2Cl_2$, 5% MeOH) 13,14-dihydro-16-(3-methylphenylamino) tetranor prostaglandin $F_1\alpha$ methyl ester is obtained as a clear oil.

Example 25

Preparation of 13,14-dihydro-16-(3-methylphenylamino) tetranor prostaglandin $F_1\alpha$:

To a 5 ml round-bottomed flask, 13,14-dihydro-16-(3-methylphenylamino) tetranor Prostaglandin $F_1\alpha$ methyl ester (0.15 mmol) and 4 mL of THF water solution (3:1, THF:$H_2O$) are added. The flask is cooled to 0° C., and excess an amount of lithium hydroxide (2.5 equiv.) is added. The ice bath is removed, and the reaction is stirred at room temperature overnight. Methylene chloride and saturated citric acid are added to the reaction mixture, and the aqueous layer is washed 3 times with methylene chloride. The organic layers are combined and washed with brine, dried ($Na_2SO_4$), concentrated, and chromatographed (methylene chloride, methanol, acetic acid, 9.6, 0.4, 0.015), to provide 13,14-dihydro-16-(3-methylphenylamino) tetranor prostaglandin $F_1\alpha$ as a clear oil.

Utilizing substantially the method of Examples 24 and 25 (and using the appropriate aniline), the following subject compounds of Examples 26–28 are obtained.

Example 26

13,14-dihydro-16-(phenylamino) tetranor prostaglandin $F_1\alpha$ methyl ester

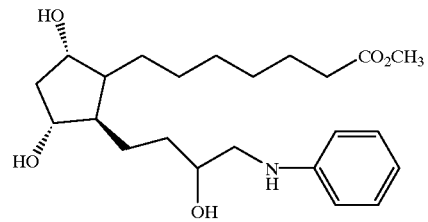

Example 27

13,14-dihydro-16-(2-methylphenylamino) tetranor prostaglandin $F_1\alpha$

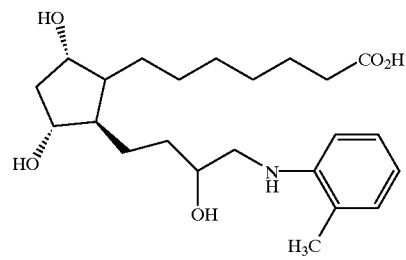

Example 28

13,14-dihydro-16-(phenylami no) tetranor prostaglandin $F_1\alpha$

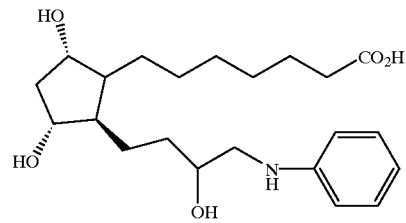

Example 29

Preparation of 13,14-dihydro-16-(3-trifluoromethylphenylthio) tetranor Prostaglandin $F_1\alpha$ 1-hydroxamic acid:

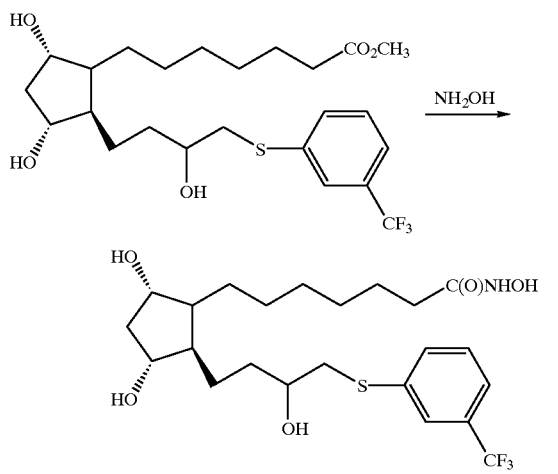

In a flame-dried 25 mL round-bottomed flask equipped with a magnetic stir bar is placed 13,14-dihydro-16-(3-trifluoromethyphenylthio) tetranor Prostaglandin $F_1\alpha$ methyl ester (Example 4) (1.0 equiv.) in methanol. To this solution is added hydroxylamine in methanol (1.25 equiv.). The solution stirred for 18 hours. The solution is then treated with 1 N hydrochloric acid and extracted with ethyl acetate. The organic layer is washed with brine, dried over anhydrous $MgSO_4$, filtered and concentrated under reduced pressure. The residue is purified by chromatography to give 13,14-dihydro-16-(3-trifluoromethylphenylthio) tetranor Prostaglandin $F_1\alpha$ 1-hydroxamic acid.

Utilizing substantially the method of Example 29 (using the appropriate hydroxylamine or sulfonamide), the following subject compounds of Examples 30–32 are obtained.

Example 30

13,14-dihydro-16-(2-fluorophenylthio) tetranor Prostaglandin $F_1\alpha$ 1-hydroxamic acid

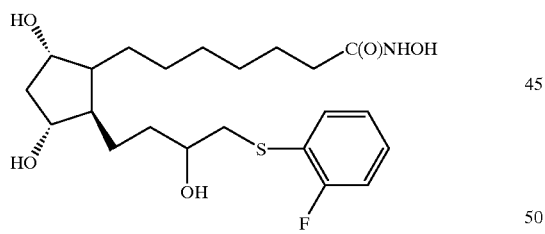

Example 31

13,14-dihydro-16-(3-chlorophenylamino) tetranor Prostaglandin $F_1\alpha$ 1-hydroxamic acid

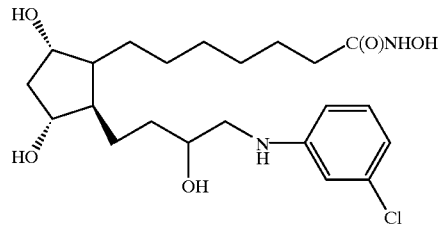

Example 32

13,14-dihydro-15-methyl-16-(2-methylphenylthio) tetranor Prostaglandin $F_1\alpha$ 1-N-methanesulfonamide

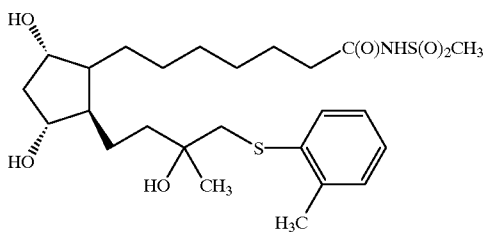

Example 33

Preparation of 13,14-dihydro-15-methylthio-15-dehydroxy-16-(N-methylphenylamino) tetranor Prostaglandin $F_1\alpha$:

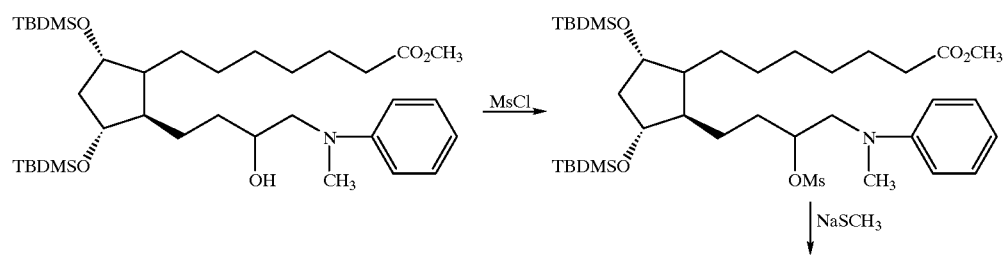

-continued

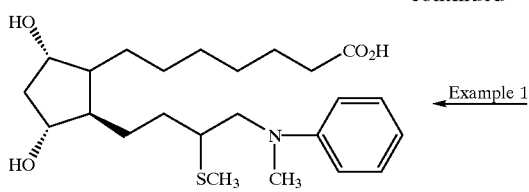 ← Example 1 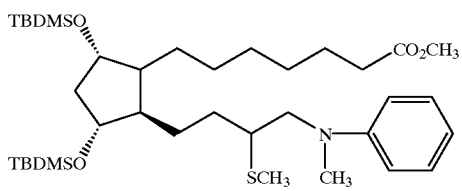

The appropriate bis-silylated compound synthesized in Example 1 is treated with methanesulfonyl chloride (1.2 equiv.) and base (1.2 equiv.) as described in the following references: E. J. Corey et al., "Simple Stereospecific Routes to 9-epi-Prostaglandin $F_2\alpha$", *J.C.S. Chem. Comm.* (1975) p. 658–9; E. J. Corey et al., "Superoxide ion as a Synthetically Useful Oxygen Nucleophile", *Tetrahedron Lett.* (1975) p. 3183–6; and references cited therein, to generate the intermediate mesylate, which is then treated immediately with nucleophiles (sodium thiomethoxide) as described in E. J. Corey et al., "Total Synthesis of 5-desoxy Leukotriene D. A New and Useful Equivalent of the 4-Formyl-Trans,Trans-1, 3-Butadienyl Anion", *Tetrahedron Lett.* Vol. 23 (1982) p. 3463–66, and references cited therein, to give 13,14-dihydro-15-methylthio-15-dehydroxy-16-(N-methylphenylamino) tetranor Prostaglandin $F_1\alpha$ after deprotection as described in Example 1.

Examples 34–36 are prepared using substantially the same procedure as that described in Example 33 (using the appropriate derivative of Formula IV). The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 34

13,14-dihydro-15-methylthio-15-dehydroxy-16-(N-methyl-phenylamino) tetranor Prostaglandin $F_1\alpha$ 1-hydroxamic acid

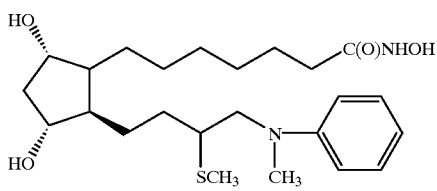

Example 35

13,14-dihydro-15-methoxy-15-dehydroxy-16-(2-fluorophenylthio) tetranor Prostaglandin $F_1\alpha$

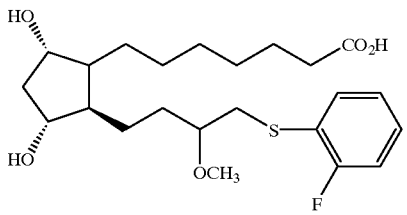

Example 36

13,14-dihydro-15-butoxy-15-dehydroxy-16-(phenylthio) tetranor Prostaglandin $F_1\alpha$ methyl ester

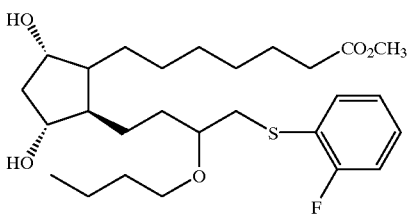

Example 37

Preparation of 13,14-dihydro-15-sulfonylmethyl-15-dehydroxy-16-(N-methylphenylamino) tetranor Prostaglandin $F_1\alpha$ methyl ester:

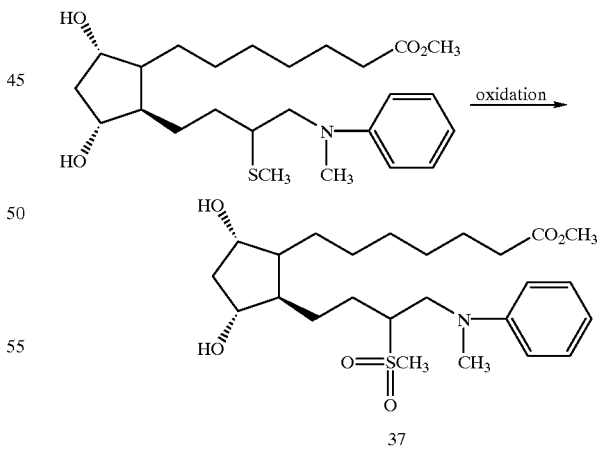

37

The methyl ester is treated with the appropriate oxidizing agent as described in the following references: E. J. Corey et al., "Total Synthesis of 5-desoxy Leukotriene D. A New and Useful Equivalent of the 4-Formyl-*Trans, Trans*-1,3-Butadienyl Anion", *Tetrahedron Lett.* Vol. 23 (1982) p. 3463–66; *Prostaglandin* Vol. 24 (1982) p. 801; Y. Girard et al., "Synthesis of the Sulfones of Leukotrienes $C_4$, $D_4$, and $E_4$", *Tetrahedron Lett.* Vol. 23 (1982) p. 1023–26; and references cited therein, or as described in Example 23.

Example 38 is prepared using substantially the same procedure as that described in Example 37 (using the appropriate derivative of Formula V). The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 38

13,14-dihydro-15-sulfoxylmethyl-15-dehydroxy-16-(N-methylphenylamino) tetranor Prostaglandin $F_1\alpha$ methyl ester

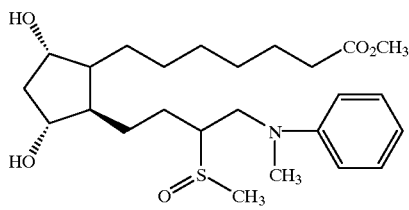

Example 39

Preparation of 13,14-dihydro-15-methyl-15-aminomethyl-16-(2-fluorophenylthio) tetranor Prostaglandin $F_1\alpha$:

rium (III) Reagents", *J. Org. Chem.* Vol. 49 (1984) p. 3904–12; T. Imamoto, et al., "Reactions of Carbonyl Compounds with Grignard Reagents in the Presence of Cerium Chloride", *J. Am. Chem. Soc.* Vol. 111 (1989) p. 4392–98; and references cited therein) gives the aminomethyl derivative, which is then transformed as described in Example 1 to give 13,14-dihydro-15-methyl-15-aminomethyl-16-(2-fluorophenylthio) tetranor Prostaglandin $F_1\alpha$.

Examples 40–42 are prepared using substantially the same procedure as that described in Example 39 (using the appropriate derivative of Formula I). The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 40

13,14-dihydro-15-methyl-15-aminomethyl-16-(2-methylphenylthio) tetranor Prostaglandin $F_1\alpha$ 1-N-methanesulfonamide

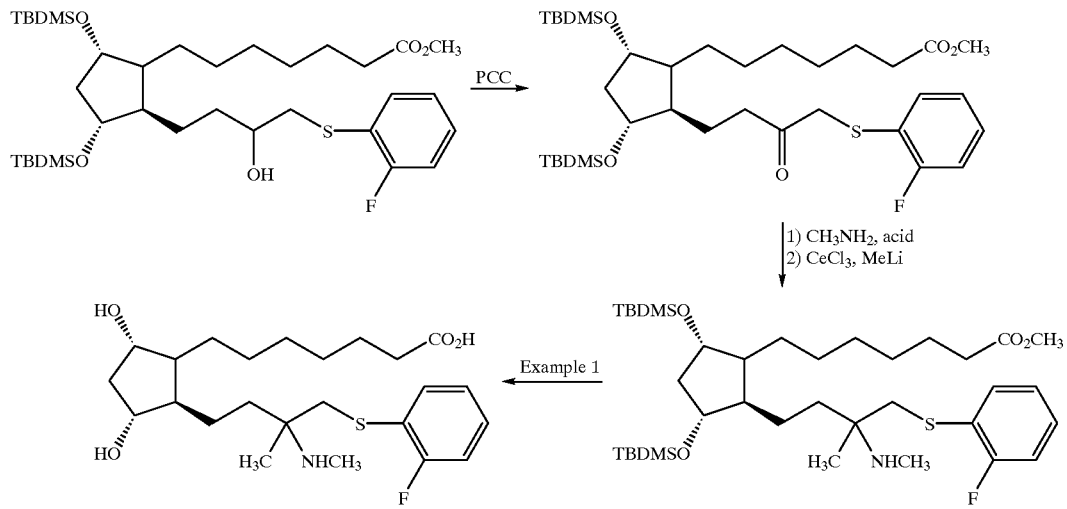

The appropriately protected derivative from Example 8 is oxidized to the ketone as described in the following references: A. McKillop and D. W. Young, "Organic Synthesis Using Supported Reagents—Part 1", *Synthesis* (1979) p. 401–22; E. J. Corey and J. W. Suggs, "Pyridinium Chlorochromate: An Efficient Reagent for Oxidation of Primary and Secondary Alcohols to Carbonyl Compounds", *Tetrahedron Lett.* Vol. 31 (1975) p. 2647–50; and references cited therein, and then condensed with N-methylamine to give the imine. Addition of the methylcerium nucleophile (~1.5 equiv.) (for examples of cerium chloride-mediated nucleophilic addition see: T. Imamoto, et al., "Carbon-Carbon Bond Forming Reactions Using Cerium Metal or Organce-

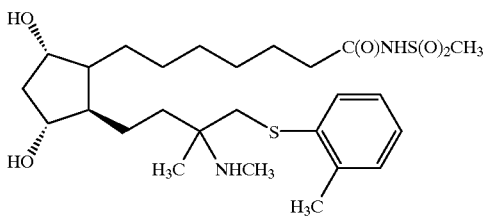

Example 41
13,14-dihydro-15-ethyl-15-aminomethyl-16-(phenylthio) tetranor Prostaglandin F₁α isopropyl ester

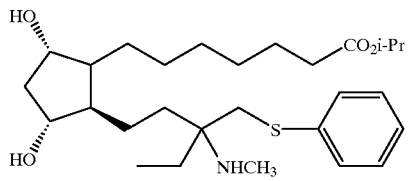

Example 42
13,14-dihydro-15-ethynyl-15-aminomethyl-16-(4-methylphenylthio) tetranor Prostaglandin F₁α isopropyl ester

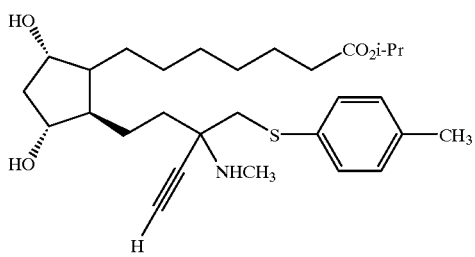

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, and osteoporosis.

The compounds of the present invention are useful in increasing bone volume and trabecular number through formation of new trabeculae, increasing bone mass while maintaining a normalized bone turnover rate, and formation of bone at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal, sublingual, and oral.

The dosage range of the compound for systemic administration is from about 0.01 to about 1000 μg/kg body weight, preferably from about 0.1 to about 100 μg/kg per body weight, most preferably from about 1 to about 50 μg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
| --- | --- |
| Compound of Example 20 | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
| --- | --- |
| Compound of Example 20 | 5 mg |
| Phosphate buffered physiological saline | 10 ml |
| Methyl Paraben | 0.05 ml |

When 1.0 ml of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
| --- | --- |
| Compound of Example 42 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2–7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

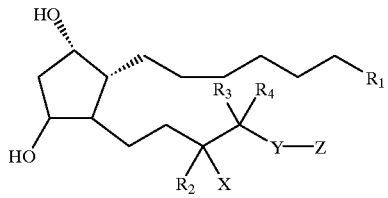

wherein
  (a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;
  (b) $R_2$ is H or lower alkyl;
  (c) X is $NR_6R_7$, $OR_8$, $SR_9$, $S(O)R_9$, or $S(O)_2R_9$; wherein $R_6$, $R_7$, and $R_8$ are independently selected from the group consisting of H, acyl, alkyl, heteroalkyl, carbocyclic aliphatic ring, heterocyclic aliphatic ring, aromatic ring, or heteroaromatic ring; and wherein $R_9$ is alkyl, heteroalkyl, carbocyclic aliphatic ring, heterocyclic aliphatic ring, aromatic ring, or heteroaromatic ring;
  (d) $R_3$ and $R_4$ are independently selected from the group consisting of H, $CH_3$, and $C_2H_5$;
  (e) Y is $NR_{10}$, S, S(O), or $S(O)_2$; wherein $R_{10}$ is H, acyl, alkyl, heteroalkyl, carbocyclic aliphatic ring, heterocyclic aliphatic ring, aromatic ring, or heteroaromatic ring;
  (f) Z is carbocyclic aliphatic ring, heterocyclic aliphatic ring, aromatic ring, or heteroaromatic ring; and
  any optical isomer, diastereomer, enantiomer of the above structure or a pharmaceutically-acceptable salt, or biohydrolyzable amide, ester, or imide thereof.

2. The compound according to claim 1 wherein $R_1$ is selected from the group consisting of $CO_2H$, $C(O)NHOH$, $CO_2CH_3$, $CO_2C_2H_5$, $CO_2C_3H_7$, $CO_2C_4H_9$, $CO_2C_3H_7O_2$, and $C(O)NHS(O)_2R_5$.

3. The compound according to claim 2 wherein $R_2$ is H or $CH_3$.

4. The compound according to claim 3 wherein X is $OR_8$ or $NR_6R_7$.

5. The compound according to claim 4 wherein Z is monocyclic.

6. The compound according to claim 5 wherein Z is aromatic ring or heteroaromatic ring.

7. The compound according to claim 6 wherein Z is thienyl or phenyl.

8. The compound according to claim 7 wherein $R_1$ is selected from the group consisting of $CO_2H$, C(O)NHOH, $CO_2CH_3$, and $CO_2C_3H_7$.

9. The compound according to claim 8 wherein X is OH.

10. The compound according to claim 9 wherein Y is S or NH.

11. The compound according to claim 10 wherein Z is substituted, said substituents being independently selected from the group consisting of halo, alkyl, haloalkyl, cyano, nitro, alkoxy, phenyl, and phenoxy.

12. The compound according to claim 10 wherein Z is substituted, said substituents being independently selected from the group consisting of halo, alkyl, cyano, and phenyl.

13. The compound according to claim 10 wherein Z is substituted; said substituents being halo or alkyl.

14. The compound according to claim 13 wherein said compound is selected from the group consisting of:

13,14-dihydro-16-(3-methylphenylthio) tetranor Prostaglandin $F_1\alpha$ methyl ester;

13,14-dihydro-16-(3-methylphenylthio) tetranor Prostaglandin $F_1\alpha$;

13,14-dihydro-16-(3-fluorophenylthio) tetranor Prostaglandin $F_1\alpha$ methyl ester;

13,14-dihydro-16-(3-fluorophenylthio) tetranor Prostaglandin $F_1\alpha$;

13,14-dihydro-16-(2,3,5,6 tetrafluorophenylthio) tetranor Prostaglandin $F_1\alpha$ methyl ester;

13,14-dihydro-16-(2,3,5,6 tetrafluorophenylthio) tetranor Prostaglandin $F_1\alpha$;

13,14-dihydro-16-(2-methylphenylthio) tetranor Prostaglandin $F_1\alpha$ methyl ester;

13,14-dihydro-16-(4-methylphenylthio) tetranor Prostaglandin $F_1\alpha$ methyl ester;

13,14-dihydro-16-(4-methylphenylthio) tetranor Prostaglandin $F_1\alpha$;

13,14-dihydro-16-(2-fluorophenylthio) tetranor Prostaglandin $F_1\alpha$ methyl ester;

13,14-dihydro-16-(2-fluorophenylthio) tetranor Prostaglandin $F_1\alpha$;

13,14-dihydro-15-methyl-16-(3-fluorophenylthio) tetranor Prostaglandin $F_1\alpha$ methyl ester;

13,14-dihydro-15-methyl-16-(3-fluorophenylthio) tetranor Prostaglandin $F_1\alpha$;

13,14-dihydro-15-methyl-16-(2-methylphenylthio) tetranor Prostaglandin $F_1\alpha$ methyl ester;

13,14-dihydro-15-methyl-16-(2-methylphenylthio) tetranor Prostaglandin $F_1\alpha$;

13,14-dihydro-16-(3-fluorophenylsulfonyl) tetranor Prostaglandin $F_1\alpha$;

13,14-dihydro-16-(3-methylphenylamino) tetranor prostaglandin $F_1\alpha$ methyl ester;

13,14-dihydro-16-(3-methylphenylamino) tetranor prostaglandin $F_1\alpha$;

13,14-dihydro-16-(2-methylphenylamino) tetranor prostaglandin $F_1\alpha$ methyl ester;

13,14-dihydro-16-(2-methylphenylamino) tetranor prostaglandin $F_1\alpha$;

13,14-dihydro-16-(2-fluorophenylthio) tetranor prostaglandin $F_1\alpha$ 1-hydroxamic acid;

13,14-dihydro-16-(3-chlorophenylamino) tetranor prostaglandin $F_1\alpha$ 1-hydroxamic acid.

15. The compound according to claim 11 wherein said compound is selected from the group consisting of:

13,14-dihydro-16-(3-trifluoromethylphenylthio) tetranor Prostaglandin $F_1\alpha$ methyl ester;

13,14-dihydro-16-(3-trifluoromethylphenylthio)tetranor Prostaglandin $F_1\alpha$;

13,14-dihydro-16-(3-trifluoromethylphenylthio) tetranor prostaglandin $F_1\alpha$ 1-hydroxamic acid.

16. The compound according to claim 10 wherein said compound is selected from the group consisting of:

13,14-dihydro-16-(phenylthio) tetranor Prostaglandin $F_1\alpha$ methyl ester;

13,14-dihydro-16-(phenylthio) tetranor Prostaglandin $F_1\alpha$;

3,14-dihydro-15-methyl-16-(phenylthio) tetranor Prostaglandin $F_1\alpha$ methyl ester;

13,14-dihydro-15-methyl-16-(phenylthio) tetranor Prostaglandin $F_1\alpha$;

13,14-dihydro-16-(phenylamino) tetranor prostaglandin $F_1\alpha$ methyl ester;

13,14-dihydro-16-(phenylamino) tetranor prostaglandin $F_1\alpha$;

13,14-dihydro-16-(2-thienylthio) tetranor prostaglandin $F_1\alpha$ methyl ester;

13,14-dihydro-16-(2-thienylthio) tetranor prostaglandin $F_1\alpha$.

17. The compound according to claim 8 wherein said compound is selected from the group consisting of:

13,14-dihydro-16-(1-napthylthio) tetranor Prostaglandin $F_1\alpha$ isopropyl ester;

13,14-dihydro-16-(1-napthylthio) tetranor Prostaglandin $F_1\alpha$;

13,14-dihydro-15-butoxy-15-dehydroxy-16-(phenylthio) tetranor prostaglandin $F_1\alpha$ methyl ester.

18. A method of treating a human or other animal subject having a bone disorder, said method comprising administering to said subject a compound according to the structure:

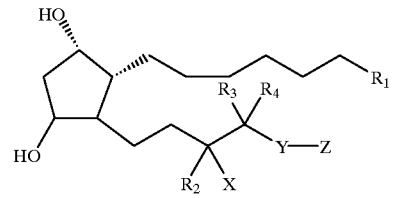

wherein (a) $R_1$ is $CO_2H$, C(O)NHOH, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;

(b) $R_2$ is H or lower alkyl;

(c) X is $NR_6R_7$, $OR_8$, $SR_9$, $S(O)R_9$, or $S(O)_2R_9$; wherein $R_6$, $R_7$, and $R_8$ are independently selected from the group consisting of H, acyl, alkyl, heteroalkyl, carbocyclic aliphatic ring, heterocyclic aliphatic ring, aromatic ring, or heteroaromatic ring; and wherein $R_9$ is alkyl, heteroalkyl, carbocyclic aliphatic ring, heterocyclic aliphatic ring, aromatic ring, or heteroaromatic ring;

(d) $R_3$ and $R_4$ are independently selected from the group consisting of H, $CH_3$, and $C_2H_5$;

(e) Y is $NR_{10}$, S, S(O), or $S(O)_2$; wherein $R_{10}$ is H, acyl, alkyl, heteroalkyl, carbocyclic aliphatic ring, heterocyclic aliphatic ring, aromatic ring, or heteroaromatic ring;

(f) Z is carbocyclic aliphatic ring, heterocyclic aliphatic ring, aromatic ring, or heteroaromatic ring; and any optical isomer, diastereomer, enantiomer of the above structure or a pharmaceutically-acceptable salt, or biohydrolyzable amide, ester, or imide thereof.

19. The method of claim 18 wherein said bone disorder is osteoporosis.

20. The method of claim 19 wherein said bone disorder is post-menopausal.

21. The method of claim 19 wherein said bone disorder is cortico-steroid induced.

22. The method of claim 18 wherein said bone disorder is osteopenia.

23. The method of claim 18 wherein said bone disorder is a bone fracture.

24. The method of claim 18 wherein said compound is administered orally.

25. The method of claim 18 wherein said compound is administered transdermally.

26. The method of claim 18 wherein said compound is administered intranasally.

27. A method of treating glaucoma, said method comprising administering to a human or other animal a safe and effective amount of a compound according to the structure:

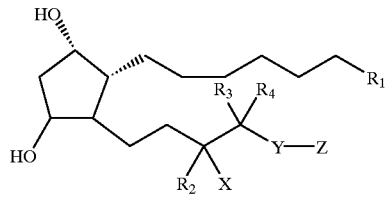

wherein (a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;

(b) $R_2$ is H or lower alkyl;

(c) X is $NR_6R_7$, $OR_8$, $SR_9$, $S(O)R_9$, or $S(O)_2R_9$; wherein $R_6$, $R_7$, and $R_8$ are independently selected from the group consisting of H, acyl, alkyl, heteroalkyl, carbocyclic aliphatic ring, heterocyclic aliphatic ring, aromatic ring, or heteroaromatic ring; and wherein $R_9$ is alkyl, heteroalkyl, carbocyclic aliphatic ring, heterocyclic aliphatic ring, aromatic ring, or heteroaromatic ring;

(d) $R_3$ and $R_4$ are independently selected from the group consisting of H, $CH_3$, and $C_2H_5$;

(e) Y is $NR_{10}$, S, S(O), or $S(O)_2$; wherein $R_{10}$ is H, acyl, alkyl, heteroalkyl, carbocyclic aliphatic ring, heterocyclic aliphatic ring, aromatic ring, or heteroaromatic ring;

(f) Z is carbocyclic aliphatic ring, heterocyclic aliphatic ring, aromatic ring, or heteroaromatic ring; and any optical isomer, diastereomer, enantiomer of the above structure or a pharmaceutically-acceptable salt, or biohydrolyzable amide, ester, or imide thereof.

28. The method of claim 27 wherein said compound is administered topically.

* * * * *